United States Patent [19]

Sussman et al.

[11] Patent Number: 5,284,472
[45] Date of Patent: Feb. 8, 1994

[54] VITREOUS CUTTER

[75] Inventors: Glenn Sussman, Lake Forest; Edward Zaleski, Santa Ana, both of Calif.

[73] Assignee: Allergan, Inc., Irvine, Calif.

[21] Appl. No.: 969,745

[22] Filed: Oct. 30, 1992

[51] Int. Cl.⁵ .............................................. A61B 17/32
[52] U.S. Cl. ...................................... 604/22; 606/171
[58] Field of Search .................. 604/22; 606/168-171; 128/751, 752, 755

[56] References Cited

U.S. PATENT DOCUMENTS

| | | | |
|---|---|---|---|
| 4,598,710 | 7/1986 | Kleinberg et al. | 606/170 |
| 4,696,298 | 9/1987 | Higgins et al. | 604/22 |
| 4,819,635 | 4/1989 | Shapiro | 128/305 |
| 4,850,354 | 7/1989 | McGurk-Burleson et al. | 604/22 |
| 4,909,249 | 3/1990 | Akkas et al. | 606/107 |
| 5,106,364 | 4/1992 | Hayafuji et al. | 604/22 |
| 5,176,628 | 1/1993 | Charles et al. | 604/22 |

Primary Examiner—C. Fred Rosenbaum
Assistant Examiner—Michael Rafa
Attorney, Agent, or Firm—Walter A. Hackler

[57] ABSTRACT

A vitreous-cutting surgical device is provided which includes a tubular sleeve having a port in a side wall thereof, proximate to a closed distal end of the tubular sleeve. A vacuum is used for drawing a portion of the vitreous to be cut from a body of vitreous into the port and a cutter sleeve, disposed within the tubular sleeve, is provided for cutting the vitreous drawn into the port. Cutting surfaces and a window in the cutter sleeve enable a preferably constant vacuum to be applied to the body of vitreous being cut during cutting thereof to eliminate, or substantially reduce, agitation of the remaining vitreous.

1 Claim, 3 Drawing Sheets

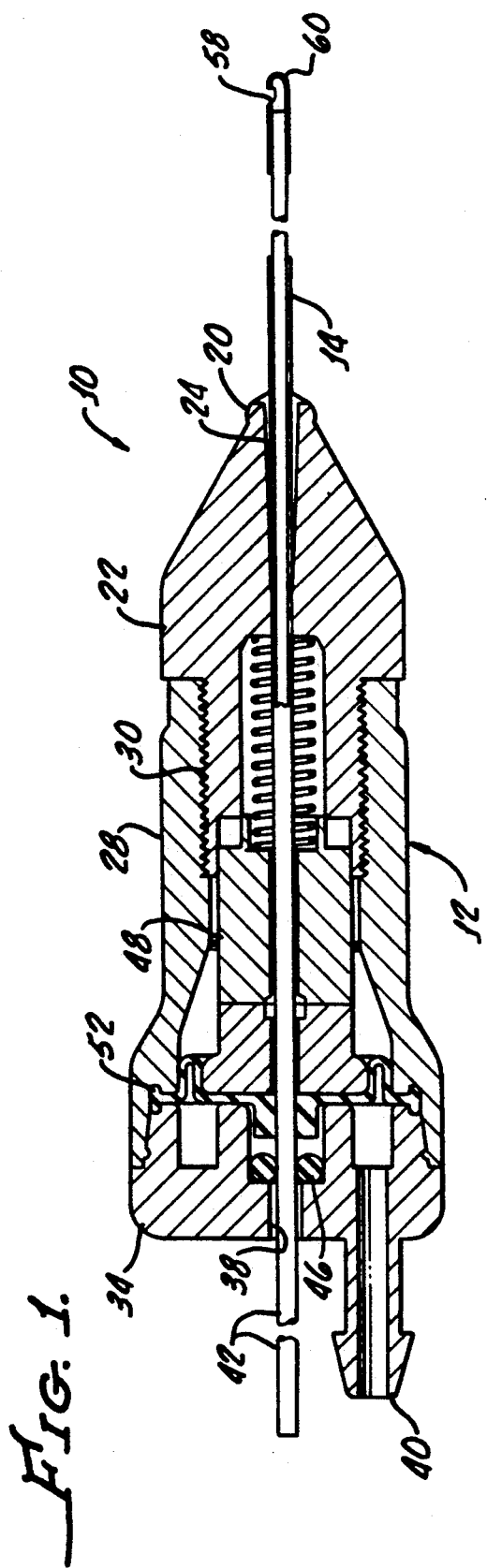
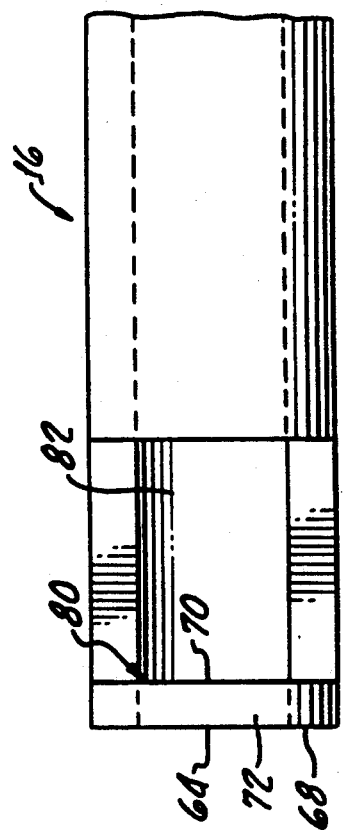
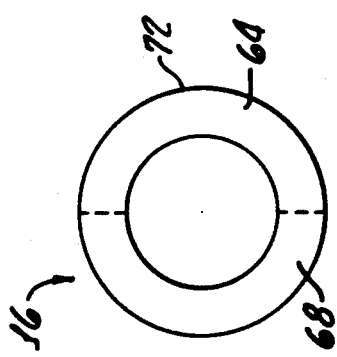

VITREOUS CUTTER

The present invention generally relates to surgical cutting instruments and more particularly to a tissue-cutting surgical device suitable for use in vitreous surgery.

Many instruments have been developed for intraocular surgery which provide for the cutting, irrigation and aspiration of vitreous and other material from an eye during intraocular surgery.

The surgery is effected by making an incision into the cornea or sclera and inserting an elongate instrument, having cutting surfaces on the distal end thereof, into the eye. The instrument typically utilizes a pair of tubas which rotate or reciprocate relative to one another in order to perform the cutting operation. An opening in provided in an outer tube proximate distal end with cutting surfaces on the inner tube for cutting the vitreous material as it is drawn through the opening by vacuum applied to the tubes.

A common problem and disadvantage of existing surgical cutters is the pulling or yanking of the vitreous material as it is being cut. This has been experienced with devices utilizing a rotation of the inner tubs with respect to the outer tube, as well as instruments which utilize a reciprocating inner tube. In other words, a vitreous bounce is created by the pull/release cycle of the instrument, which is caused by sucking in of vitreous and then closing of the opening during cutting of the vitreous drawn inside the outer tube. Unfortunately, this agitation of the vitreous is translated to the retina. More severe agitation of the retina naturally occurs when the cutting instrument approaches the retina during cutting of vitreous humor.

The apparatus and method of the present invention overcome the disadvantages of prior art devices and provide a means for agitation-free removal of vitreous humor or strands.

SUMMARY OF THE INVENTION

The present invention generally includes a tubular sleeve having means for defining a port in a side wall thereof proximate a closed distal end of the tubular sleeve. A vacuum provides means for drawing a portion of the vitreous to be cut from a vitreous body into the port, and means are provided for cutting the tissue portion from the vitreous body without substantial recoil of the remaining vitreous body from the opening.

Hence, the surgical device, in accordance with the present invention, enables the cutting of portions of the vitreous body without substantial agitation of the vitreous body, as hereinabove described in connection with prior art devices.

More particularly, means are provided for maintaining vacuum on the vitreous body during cutting of the vitreous portion. Because the vacuum is maintained on the vitreous during and after the cutting cycle, there is no pulsing of a vacuum cycle on the vitreous body which causes the agitation thereof, such as occurs in the prior art devices hereinabove described.

More particularly, the means for cutting the vitreous comprises a cutter sleeve slidably disposed within the tubular sleeve, which includes opposite facing cutting surfaces formed into a distal end of the cutter sleeve.

Of these cutting surfaces, a first is disposed on the cutter sleeve distal end on a portion of the cutter sleeve circumference facing the tubular sleeve port. A second of the surf aces is disposed on a perimeter of a window formed into the cutting sleeve. The aforementioned window provides a means for maintaining vacuum on the vitreous body during the cutting of a portion therefrom.

A driver assembly is also provided in accordance with the present invention for supporting the tubular sleeve at the distal end thereof and a piston means, disposed in the driver assembly and attached to the cutter sleeve, for causing reciprocal movement of the cutter sleeve within the tubular sleeve. Preferably, the tubular sleeve port and the cutter sleeve window are sized for enabling substantially constant vacuum to be drawn on the body of vitreous during cutting of the vitreous portion.

The method in accordance with the present invention for cutting vitreous generally includes the steps of applying a vacuum to vitreous in order to draw a portion of the vitreous away from a remainder of the vitreous body, cutting the portion of the vitreous away from the remainder of the vitreous, and maintaining a vacuum on the remainder of the vitreous during cutting of the portion of the vitreous. This process enables the cutting of the portion of the vitreous from the remainder of the vitreous without severe agitation or bouncing of the vitreous remainder during the cutting process.

More particularly, the step for maintaining a vacuum includes the maintenance of a substantially constant vacuum on the remainder of the vitreous during the cutting of the vitreous portion therefrom.

BRIEF DESCRIPTION OF THE DRAWINGS

The advantages and features of the present invention will be better understood by the following description when considered in conjunction with the accompanying drawings in which:

FIG. 1 in a cross-sectional view of a surgical device in accordance with the present invention, generally showing a driver assembly, a tubular sleeve, and a cutting sleeve disposed therein;

FIGS. 2a and 2b are end and side views, respectively, of the distal end of a cutter sleeve in accordance with the present invention;

DETAILED DESCRIPTION

Figure 3A:
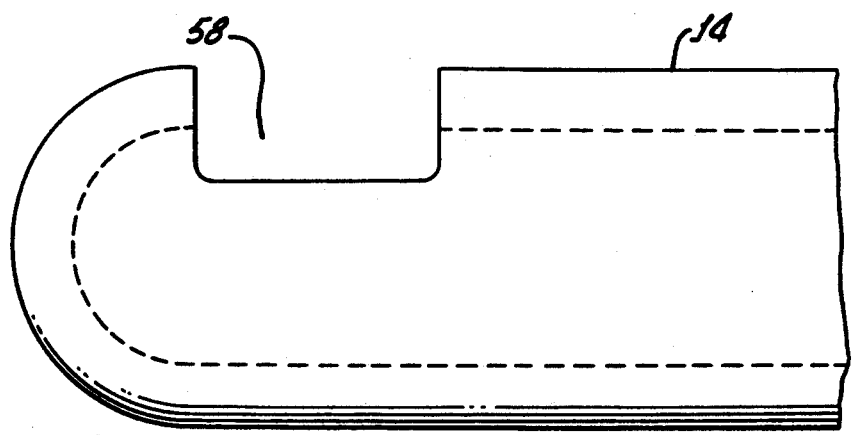
FIGS. 3a and 3b are side and top views, respectively, of a distal end of the tubing sleeve in accordance with the present invention.

Turning now to FIG. 1, there is shown a vitreous-cutting surgical device 10, in accordance with the present invention, which generally includes a driver assembly 12, a tubular sleeve 14, and a cutter sleeve 16. Materials construction for the driver assembly 12, tubular sleeve 14, and a cutter sleeve 16 may be of plastic or metal or combinations thereof, all suitable for use in surgical applications.

The tubular sleeve 14, which may extend several centimeters or more from a front 20 of the driver assembly 12, is fixed to a driver assembly nut 22 by means of an epoxy resin 24, or the like. The nut 22 is secured to a driver assembly body 28 by means of threads 30. The body 28 is, in turn, fixed to a cap 34 which includes openings 38, 40 for a vacuum line 42 and a pressure source (not shown).

An O ring 46 provides a seal and a piston 48 is suspended within the body 28 by means of a diaphragm 52. The piston 48 is slidably mounted within the body 28 and nut 22 and provides means for causing reciprocating movement within the body 28 of the driver assembly 12.

A spring 54 provides a biassing action against the piston 48 in a rearward direction away from the front 20 of the driver assembly 12. An pulsed pressure is provided through the opening, the diaphragm 52 and piston 48 move forward and thereafter rearward due to the action of the spring 54. Typical pressure applied to the diaphragm 52 and piston 48 is approximately 30 pounds per square inch and somewhere between 1 and 600 cycles per minute, or more, causing reciprocation of the piston 48 within the body 28, of between 0 and 600 cycles per minute.

The cutter sleeve 16 is interconnected with the piston 48 and vacuum line 42 for reciprocation therewith inside the tubular sleeve 14. A vacuum applied to the line 42 causes the vitreous (not shown in FIG. 1) to be drawn into a port 58 proximate a distal end 60 of the tubular sleeve 14. The port 58 is in vacuum communication through the cutter sleeve 16 and tubular sleeve 14 with the vacuum line 42 with the latter providing a means for maintaining vacuum on the body of the vitreous during cutting of the vitreous portion, as hereinafter described.

Turning now to FIGS. 2a and 2b, a distal end 64, the cutting sleeve 16, includes opposite facing cutting surfaces 68, 70 which provide a means for cutting the vitreous portion (not shown in FIGS. 2a and 2b) from a vitreous body (not shown in FIGS. 2a and 2b) after the portion is drawn through the tubular sleeve port 58 as will be hereinafter described in greater detail.

Figure 3B:
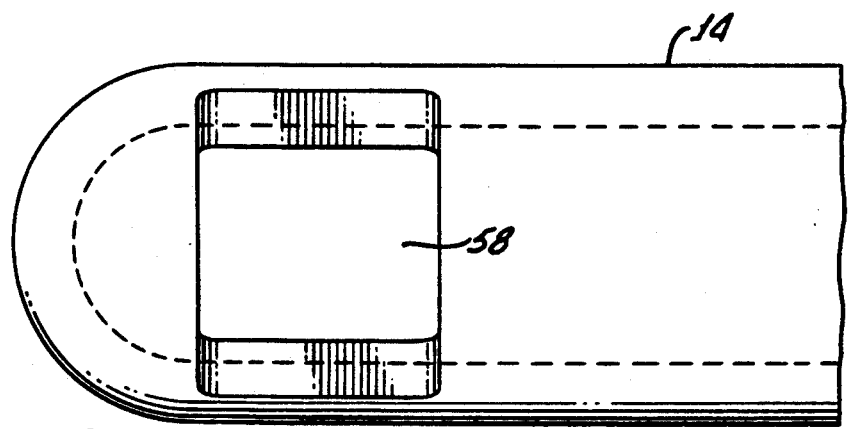

The cutting surface 68 is the first of the opposite facing surfaces 68, 70 and is disposed directly on the distal end 64 of the cutter sleeve 16 on a portion 72 of a circumference 76 facing the tubular sleeve port 58 (see FIGS. 3a and 3b).

Cutting surface 70 is the second of the opposing cutting surfaces 68, 70 and is disposed on a perimeter 80 of a window 82 in the cutting sleeve 16 facing the tubular sleeve port 58.

The port 58 in the distal and of the tubular sleeve 14 is more clearly shown in FIGS. 3a and 3b. During operation, as hereinafter discussed in greater detail, a portion of vitreous body (not shown in FIGS. 3a and 3b) is drawn through the port 58 by application of vacuum through the line 42.

Figure 4A:
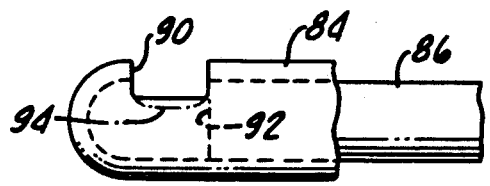
FIGS. 4a and 4b illustrate a prior art cutting device.
Figure 4B:
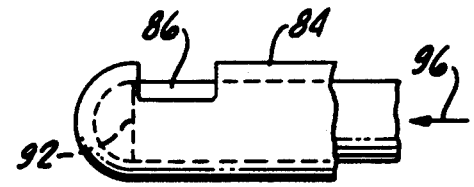
Figure 6A:
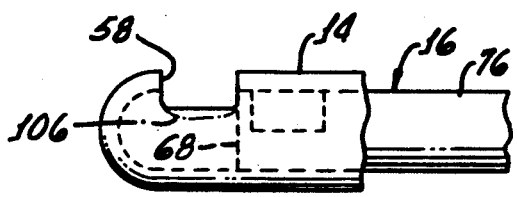
FIGS. 6a and 6b illustrate the cutting action of the tubular sleeve and cutting sleeve in accordance with the present invention.
Figure 6B:
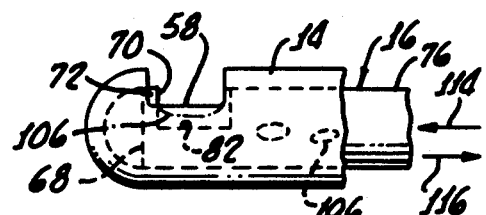

For comparison and clarity in describing the present invention, there is shown in FIGS. 4a and 4b a prior art device having an outer sleeve 84, an inner cutting sleeve 86 with the outer sleeve 84 having a port 90 therein, and the inner cutting sleeve 86 having a single cutting surface 92 thereon.

Figure 5A:
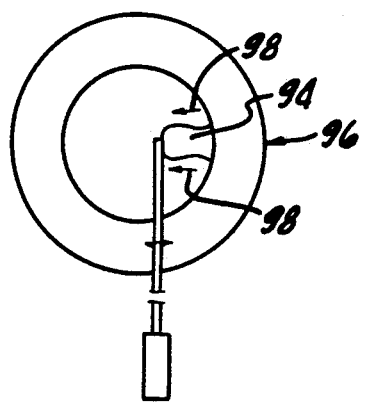
FIGS. 5a, 5b and 5c illustrate the agitation on a vitreous caused by a cutting thereof with a prior art device.
Figure 5B:
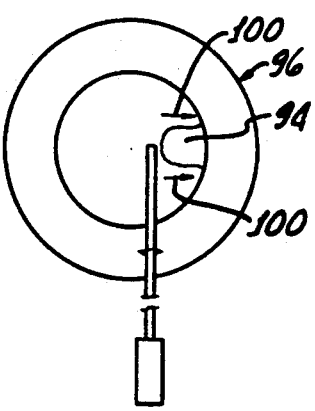
Figure 5C:
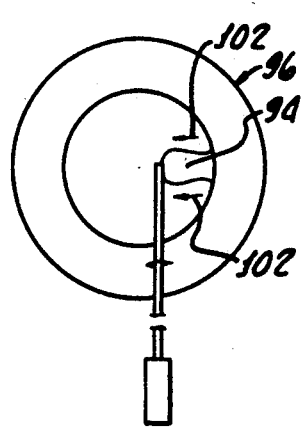

In operation, as illustrated in FIGS. 5a, 5b and 5c, in one prior art device, a vacuum is drawn through the opening 90 to draw vitreous 94 into the opening 90 for subsequent cutting by the edge 92 as the inner sleeve 86 is moved in the direction of arrow 96, as shown in FIG. 4b. The vacuum or suction of the vitreous 94 into the opening 90 causes a movement of the vitreous 94 in the direction of arrow 98 (see FIG. 5a).

When the inner sleeve 86 is moved forward to cut all of the vitreous 94, as shown in FIG. 5b, the opening 90 is closed, thereby stopping suction on the vitreous 94.

Due to the resilient nature of the vitreous 94 and its adhesion to surfaces within an eye 96, when the inner sleeve 86 seals the port 90, the vitreous 94 draws away from the port 90 as indicated by the arrows 100 in FIG. 5b. When the inner sleeve 86 is moved in a reciprocating manner away from the port 90, vacuum again is applied to the vitreous 94, causing abrupt movement thereof towards the port 90 as indicated by the arrows 102 in FIG. 5c.

Clearly, this operation of prior art necessarily causes agitation of the vitreous material 94.

This structure and function is to be compared to the structure and function of the present invention, as shown in FIGS. 6a, 6b and 7a-7c. As illustrated, when suction is drawn, a portion 106 of a body of vitreous 108 within an eye 110, for example, is drawn into the port 58.

Figure 7A:
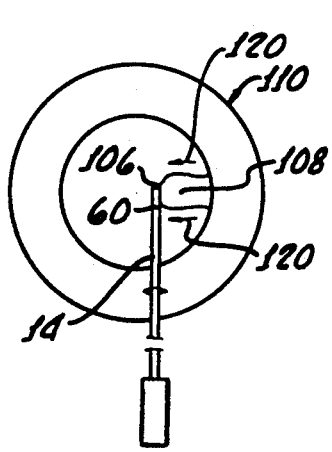
FIGS. 7a, 7b and 7c illustrate the cutting action of the surgical device in accordance with the present invention on vitreous without agitation, pulsation, or bounce thereof due to the cutting action of the surgical device.
Figure 7B:
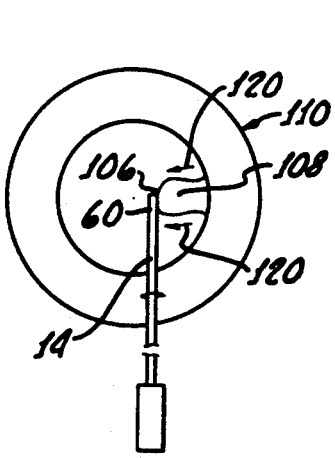
Figure 7C:
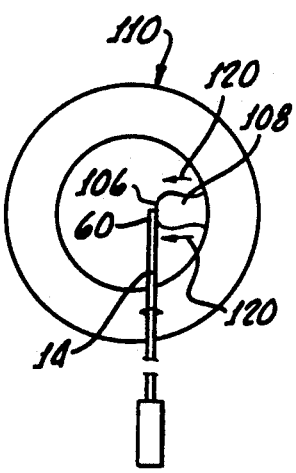

Upon movement of the cutter sleeve 16 in the direction of arrow 114, the first cutting surface 68 severs the vitreous portion 106 while the window 82 in the cutter sleeve enables vacuum to be maintained on the vitreous body 108, thus continuing to pull vitreous portions 106 into the port 58. Upon reverse or reciprocal movement of the cutter sleeve 16 in the direction of arrow 116, the second cutting surface removes portions 106 from the vitreous body 108. Since vacuum is continually applied to the vitreous body, movement thereof towards the distal ends 60 of the sleeve, as represented by the arrows 120 in FIGS. 7a, 7b, and 7c, is preferably constant, thereby eliminating, or substantially reducing, agitation of the vitreous body 108 during cutting thereof, in contrast to the bouncing action caused by the prior art device, as shown in FIGS. 5a-5c.

The consistency of vacuum through the opening 58 is consequently dependent upon the size of the port 58 in the tubular sleeve 14 and the window 82 in the cutter sleeve 16. Preferably, these openings are approximately equal in order to provide a constant vacuum force on the vitreous 108 during the cutting thereof.

Accordingly, a method in accordance with the present invention generally includes the step of applying a vacuum to vitreous in order to draw a portion 106 of the vitreous away from the remainder 108 of the vitreous and thereafter cutting the portion 106 of the vitreous away from the remainder 108 of the vitreous, while maintaining a vacuum on the remainder 108 of the vitreous during cutting of the portion 106. With proper sizing of the ports 58 and window 82, a substantially constant vacuum may be applied to the remainder 108 of vitreous during cutting of the portion 106.

Although there has been hereinabove described a specific arrangement of a tissue-cutting surgical device, intended for cutting vitreous in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope and spirit of the present invention an defined in the appended claims.

What is claimed is:

1. A vitreous-cutting surgical device comprising:

a tubular sleeve having means for defining a port in a side wall thereof proximate a closed distal end of said tubular sleeve;

vacuum means for drawing a portion of vitreous to be cut from a body of vitreous into said opening;

means for cutting the vitreous portion from the body of vitreous, said means for cutting vitreous comprising a cutter sleeve slidably disposed within said tubular sleeve, said cutter sleeve comprising opposite facing cutting surfaces formed into a distal end of the cutter sleeve, a first of said opposite facing cutting surfaces being disposed on the cutter sleeve distal end on a portion of a cutter sleeve circumference facing the tubular sleeve port and a second of said opposite facing cutting surfaces being disposed on a perimeter of the window formed into the cutting sleeve;

means for maintaining vacuum on said body of vitreous during cutting of the vitreous portion, said means for maintaining vacuum comprises a window formed into the cutting sleeve proximate the distal end thereof, said window facing the tubular sleeve port, said window being in vacuum communication through the cutting sleeve with the vacuum means, the tubular sleeve port and the cutter sleeve window being of equal area for enabling substantially constant vacuum to be drawn on said body and vitreous during cutting of the vitreous portion; and driver assembly means for supporting said tubular sleeve at a proximal end thereof and piston means, disposed in said driver assembly means and attached to said cutter sleeve, for causing reciprocal movement of the cutter sleeve within the tubular sleeve.

* * * * *